United States Patent

Masini et al.

[11] Patent Number: 5,198,121
[45] Date of Patent: Mar. 30, 1993

[54] DRYING OF HYDROCARBON/HYDROCHLORIC ACID/WATER ADMIXTURES

[75] Inventors: Jean-Jacques Masini, Chaponost; Elie Ghenassia, Grenoble; Raymond Commandeur, Vizille; Rene Clair, Martigues; Jean-Louis Guillaumenq, Port De Bouc, all of France

[73] Assignee: Atochem, Puteaux, France

[21] Appl. No.: 797,159

[22] Filed: Nov. 26, 1991

Related U.S. Application Data

[63] Continuation of Ser. No. 480,960, Feb. 16, 1990, abandoned.

[30] Foreign Application Priority Data

Feb. 16, 1989 [FR] France .................. 89 02024

[51] Int. Cl.$^5$ .................................... C02F 1/28
[52] U.S. Cl. .................................... 210/689; 34/9; 55/35; 570/211; 570/239; 570/262; 585/820; 585/823; 585/824
[58] Field of Search .............. 34/9; 55/29, 31, 33, 55/35; 585/823, 824, 820; 210/679, 689; 570/239, 262

[56] References Cited

U.S. PATENT DOCUMENTS

| | | | |
|---|---|---|---|
| 2,203,144 | 6/1940 | Hammond | 55/33 |
| 2,888,494 | 5/1959 | Kissling | 570/239 |
| 3,267,644 | 8/1966 | Jacobowsky | 55/33 |
| 4,145,260 | 3/1979 | Steele et al. | 470/262 |
| 4,307,260 | 12/1981 | Moore et al. | |
| 4,418,233 | 11/1983 | Danz et al. | 570/239 |
| 4,663,052 | 5/1987 | Sherman et al. | 210/689 |

OTHER PUBLICATIONS

Kirk-Othmer, *Concise Encyclopedia of Chemical Technology*, 1985, pp. 374-375.

Primary Examiner—Wilbur Bascomb, Jr.
Assistant Examiner—Neil M. McCarthy
Attorney, Agent, or Firm—Burns, Doane, Swecker & Mathis

[57] ABSTRACT

Water-containing mixtures of at least one hydrocarbon/halocarbon and hydrochloric acid, e.g., the methyl chloride feedstream in conventional process for the synthesis of chloromethanes, are desiccated by intimately contacting such mixtures with an effective drying amount of an essentially anhydrous drying agent that includes (i) a metal sulfate, chloride or perchlorate, or (ii) phosphorus pentoxide.

1 Claim, 1 Drawing Sheet

DRYING OF HYDROCARBON/HYDROCHLORIC ACID/WATER ADMIXTURES

This application is a continuation of application Ser. No. 07/480,960, filed Feb. 16, 1990 now abandoned.

BACKGROUND OF THE INVENTION

1. Field of the Invention

The present invention relates to the drying of water-containing hydrocarbons, notably those hydrocarbons used in the production of chloromethanes.

This invention especially relates to the drying of optionally halogenated hydrocarbons which contain both water and hydrochloric acid.

2. Description of the Prior Art

The drying of perchloroethylene using a solution of calcium chloride (*Chem. Abstracts*, Vol. 99,177849d) and in the absence of hydrochloric acid is known to this art. The drying of chloroform $CHCl_3$ and carbon tetrachloride $CCl_4$, after purification thereof by extraction with water (*Chem. Abstracts*, Vol. 62,2227e), with calcium chloride ($CaCl_2$), but always in the absence of hydrochloric acid, is also known to this art.

Nonetheless, serious need exists in this art for a technique to dry hydrocarbons containing hydrochloric acid and water without concomitantly removing the hydrochloric acid. This problem is particularly acute in the synthesis of chloromethanes as they exit the chlorination reactor, where the chloromethanes are mixed with hydrochloric acid (in each instance that a hydrogen atom is substituted by a chlorine atom, one mole of hydrochloric acid is formed as a by-product) and with water which is introduced into the process as an impurity in the starting materials. In such process the water must be removed to prevent its accumulation and also to avoid clogging or blocking the pipelines with ice and hydrates. The hydrochloric acid is recovered and is then reclaimed by conversion into chlorine in a Deacon reaction or an oxychlorination reaction. If water is removed from this mixture of chloromethanes by condensation, then there is a risk, due to the great solubility of hydrochloric acid in water, of producing a solution of hydrochloric acid in water which is subsequently difficult to separate There is a risk that the disadvantage will be the same if it is desired to separate the water from this mixture using a drying agent.

Surprisingly, it has now unexpectedly been determined that hydrocarbons containing hydrochloric acid and water can be selectively dried, while retaining only water on the drying agent.

SUMMARY OF THE INVENTION

Accordingly, a major object of the present invention is the provision of a novel process for drying a mixture containing at least one hydrocarbon, hydrochloric acid and water, comprising contacting such mixture with a drying agent selected from among (i) anhydrous metal sulfates, chlorides or perchlorates or (ii) phosphorus pentoxide, until the drying agent has sorbed a major proportion of the water.

BRIEF DESCRIPTION OF THE DRAWING

The FIGURE of Drawing is a schematic/diagrammatic representation of a preferred embodiment of the process/apparatus according to the present invention.

DETAILED DESCRIPTION OF THE PREFERRED EMBODIMENTS OF THE INVENTION

Figure 1:
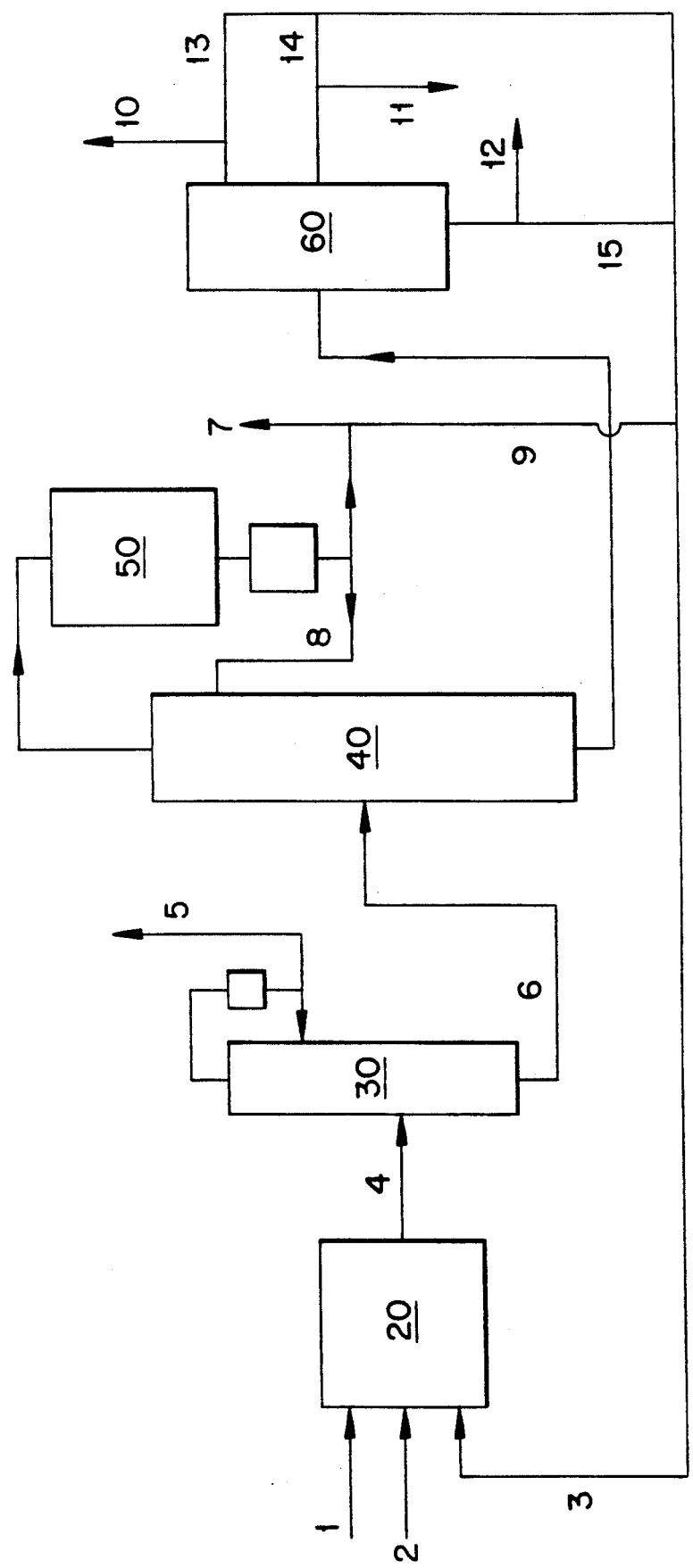

More particularly according to the present invention, although it is applicable for the drying of any hydrocarbon, it is advantageously employed to dry benzene and the alkylated or polyalkylated derivatives thereof, namely, benzene substituted by one or more linear or branched hydrocarbon chains, each containing up to 8 carbon atoms. Benzene, toluene, xylene, isopropylbenzene, styrene and ethylbenzene are exemplary of the hydrocarbons that can be dried according to the invention. The halogenated hydrocarbons can likewise be dried per the present invention.

The halogenated hydrocarbon may contain fluorine, chlorine or bromine atoms, or two or three of such substituents and it may be saturated or unsaturated, that is to say, it may comprise one or more double bonds or one or halogenated hydrocarbon preferably has from 1 to 4 carbon atoms. The invention is particularly useful for the drying of chloromethanes and chlorinated hydrocarbons containing two carbon atoms. Exemplary chlorinated hydrocarbons containing two carbons are 1,2-dichloroethane, vinyl chloride, 1,1,1-trichloroethane, 1,1,2-trichloroethane, trichloroethylene and perchloroethylene. The halogenated hydrocarbon may be a mixture of a number of halogenated hydrocarbons; it may also comprise a solvent solution thereof. The amount of hydrochloric acid is immaterial, as is the amount of water. However, the amount of water is advantageously less than 1% by weight and preferably less than 0.1%.

The presence of greater amounts of water in the hydrocarbon is also envisaged by the present invention, but the invention would no longer be economically viable. Indeed, in the event of amounts essentially on the order of a few percent, or more, it is simpler to employ conventional separations such as distillation or an extraction, and then to carry out the process of the invention.

The mixture treated may be gaseous, or liquid, or partially gaseous. The temperature and the pressure of the process are not critical. Thus, the process of the invention can be used to dry the starting mixture whatever the temperature and pressure available, and without having to modify the temperature/pressure. The mixture may also contain other constituents, for example chlorine.

The drying agent (desiccant) is in solid form and can be easily separated from the mixture. It can be in the form of powder or of granules in a stationary bed or a fluid bed. It is a product, the function of which is to sorb only water, but neither hydrochloric acid nor optionally chlorine when it is present and, of course, not the halogenated hydrocarbon. It is an anhydrous salt which quite obviously must not react chemically with hydrochloric acid. Metal sulfates, chlorides and perchlorates are suitable. It is possible to use, for example, calcium sulfate, sodium sulfate, copper sulfate, zinc chloride, calcium chloride, barium perchlorate or magnesium perchlorate.

Calcium chloride is advantageously employed. The amount of the drying agent depends on the amount of water than can be tolerated which is to remain in the mixture.

A calcium chloride having a water content ranging from 0% to 25% by weight and, preferably, from 0% to 12%, is preferably used.

To produce a mixture containing not more than a few ppm of water, it is necessary to use an essentially anhydrous drying agent. For example, to provide a mixture containing not more than 10 ppm of water, it is preferred to use a calcium chloride having a water content of less than 5% by weight.

The amount of the drying agent depends on the total amount of water sought to be sorbed. For example, when a stationary bed is used, the drying agent in closest proximity to the inlet of the flow of mixture to be dried, first becomes saturated with water, and this saturation progresses through the depth of the entire bed. To ensure proper drying (desiccation), it suffices that adequate anhydrous drying agent, not yet saturated with water, should remain present. The residence time of intimate contact of the mixture to be dried with the drying agent is also not critical. It is advantageously less than 10 minutes and preferably ranges from 1 to 5 minutes. Employing much longer residence times is also within the scope of the invention, but this is not necessary to obtain satisfactory results.

Lengthy residence times correspond to a large volume of drying agent. This is a good precaution for assuring proper drying, but such large volume can effect pressure drops which are incompatible with the other parameters of the process. One skilled in this art can very easily determine the best compromise among the variables.

The present invention also features a process for the synthesis of chloromethanes by intimately contacting a mixture containing at least one chloromethane, hydrochloric acid and water, at any point in the process, with a drying agent selected from among (i) anhydrous metal sulfates, chlorides or perchlorates or (ii) phosphorus pentoxide.

The synthesis of chloromethanes comprises preparing methyl chloride ($CH_3Cl$) and then, by chlorination, the higher chloromethanes: methylene chloride ($CH_2Cl_2$), chloroform ($CHCl_3$) and carbon tetrachloride ($CCl_4$). $CH_3Cl$ is prepared by chlorination of methane or by hydrochlorination of methanol. Such $CH_3Cl$, optionally containing a proportion of the higher chloromethanes, is then chlorinated using liquid or gaseous chlorine. At the outlet of the chlorination reactor, a mixture of chloromethanes, hydrochloric acid, trace amounts of water and possibly a minor amount of chlorine is recovered.

The water is neither a reactant nor a reaction product, but is present as an impurity in the starting materials such as chlorine, and a fraction of it can remain in the $CH_3Cl$ emanating from the methanol hydrochlorination reaction.

The HCl is separated by distilling this mixture through the "HCl column". Advantage is thus taken of a favorable concentration profile of the traces of chlorine in this column to exhaust such trace amounts of chlorine, for example with the aid of UV lamps, by completing the chlorination. A mixture of chloromethanes, water and a minor fraction of hydrochloric acid which is poorly separated in the HCl column is provided as tailings. This mixture is subjected to a series of distillations to separate the various chloromethanes which constitute the desired final product and a fraction thereof is recycled to the chlorination reactor to adjust the proportions of the various chloromethanes.

In a first column (downstream of the HCl column), designated a "methyl chloride column", the $CH_3Cl$ and the major proportion of the water are taken off overhead, together with the trace amounts of HCl and of chlorine which were still present after treatment in the HCl column. At the base of this $CH_3Cl$ column a mixture of higher chloromethanes is present which in turn is separated into its various components by distillation. Although its boiling point is higher than that of the higher chloromethanes, the trace amounts of water exit overhead because of various partial azeotropes and of the formation of more or less stable $CH_3Cl$ hydrates.

Such a process for the synthesis of chloromethanes is described in EP 128,818, GB 2,158,067, GB 2,181,132 and GB 1,456,568, assigned to the assignee hereof. The invention is advantageously applied to methyl chloride produced by hydrochlorination of methanol or by chlorination of methane and to the $CH_3Cl$ originating from the $CH_3Cl$ column, either to the entire flowstream or only to the proportion recycling to the chlorination reactor. The benefits of the invention include the removal of water to prevent accumulation thereof in the process and also the prevention of corrosion problems. Indeed, the simultaneous presence of water, of HCl and possibly of chlorine at the head of the $CH_3Cl$ column promotes corrosion. In a preferred embodiment of the invention, the mixture exiting overhead from the $CH_3Cl$ column is dried upstream of the condenser and the reflux vessel. This preferred embodiment of the invention is illustrated in the attached FIGURE of Drawing, and includes a chlorination reactor 20, an HCl separation column 30, a $CH_3Cl$ column 40, means 50 for carrying out the drying according to the invention and means 60 for separating the higher chloromethanes. The $CH_3Cl$ emanating from the hydrochlorination reaction (not shown) is introduced via line 1, the chlorine via line 2 and the recycled chloromethanes via line 3. The output 4 is distilled in column 30 and the HCl is collected at 5 and the tailings, containing the chloromethanes, water and a slight fraction of HCl, are fed into the column 40 via the line 6. Line 7 indicates the output of $CH_3Cl$, 8 the reflux and 9 the recycle. The higher chloromethanes are separated in vessel 60; conduits 10, 11 and 12 represent the output of $CH_2Cl_2$, $CHCl_3$ and $CCl_4$, respectively. Conduits 9, 13, 14 and 15 indicate the transport of $CH_3Cl$, $CH_2Cl_2$, $CHCl_3$ and $CCl_4$, which are combined in the flowstream 3 and are recycled to the reactor 20.

The drying agent (desiccant) is preferably calcium chloride. The mixture to be dried exiting overhead from the $CH_3Cl$ column is at a temperature ranging from 5° C. to 60° C. and preferably from 20° to 50° C. Its pressure advantageously ranges from 1 to 10 bars absolute.

The amount of water can vary over wide limits; it is advantageously less than 0.5% by weight and preferably ranges from 50 to 500 ppm. The amount of HCl depends on the efficiency of the HCl separation column; it is generally less than 1,000 ppm and preferably ranges from 50 to 500 ppm.

The overhead mixture from the $CH_3Cl$ column which is to be dried may also contain chlorine. The concentration of such chlorine values varies according to the efficiency of the chlorination reactor and of the optional finishing reaction which may be carried out in the HCl column. This concentration may attain values of up to 10,000 ppm.

The $CH_3Cl$ separation column may be coupled with the $CH_2Cl_2$ separation column, or a single column may be used having an overhead outlet of $CH_3Cl$ and the higher chloromethanes at various side outlets, or any combination of this same type, which is well known to the distillation art. It is also within the ambit of the present invention to arrange the drier at the head of this column on the gaseous phase consisting essentially of methyl chloride.

In order to further illustrate the present invention and the advantages thereof, the following specific examples are given, it being understood that same are intended only as illustrative and in nowise limitative.

EXAMPLE 1

A drier was constituted of a glass column 0.5 m in height and 0.45 m in diameter, which was filled with 30 kg of $CaCl_2$ granules of 3 to 8 mm over a height of 37.5 cm. The water content of the $CaCl_2$ was 2.3%. A flow-stream of gaseous $CH_3Cl$ containing HCl, water and chlorine was passed through this bed, from the bottom upwards, this being carried out over 408 hours. The results are reported in Table I.

TABLE I

| Pressure (bar absolute) | Time (h) | Residence time | $(H_2O)$ i | ppm o | $(Cl_2)$ i | ppm o | (HCL) i | ppm o |
|---|---|---|---|---|---|---|---|---|
| 1 | 170 | 4 | 70 to 105 | <25 | 85 | 85 | 300 | 300 |
| 1 | 180 | 4 | 900 | <30 | 500 | 490 | 300 | 290 |
| 1 | 190 | 4 | 300 | <30 | 550 | 500 | 350 | 380 |
| 1 | 211 | 4 | 300 | <30 | 1,050 | 1,050 | 350 | 350 |
| 1 | 265 | 4.5 | 310 | 25–30 | 950 | 980 | 300 | 290 |
| 1 | 297 | 3.5 | 300 | <25 | 950 | 980 | 500 | 460 |
| 1.1 | 376 | 4 | 150 | <25 | | | | |
| 1.5 | 383 | 4.5 | 190 | <25 | 950 | 980 | 500 | 460 |
| 1 | 408 | 5.3 | 300 | <25 | 2,100 | 2,000 | 350 | 350 | i = drier inlet
o = drier outlet
The residence time was calculated for the empty drier.

EXAMPLE 2

The operation of Example 1 was repeated, but with the drier charged (starting from the bottom towards the top of the bed) with:

7 kg of $CaCl_2$ containing 22% of water
5 kg of $CaCl_2$ containing 12% of water
8 kg of $CaCl_2$ containing 21.5% of water
8 kg of $CaCl_2$ containing 10% of water
2 kg of $CaCl_2$ containing 12% of water.

The operation was carried out in this manner for 32 hours and then a breakthrough of the bed was observed.

The results are reported in Table II.

TABLE II

| Time (h) | Residence time (min) | $(H_2O)$ i | ppm o | $(Cl_2)$ i | ppm o | (HCl) i | ppm o |
|---|---|---|---|---|---|---|---|
| 0 | 4.6 | 520 | 130 | 1,100 | 1,050 | 300 | 300 |
| 10 h, 30 min | 4.6 | 520 | 130 | 1,100 | 1,050 | 300 | 300 |
| 13 | 4.6 | 350 | 120 | 1,100 | 1,050 | 300 | 300 |
| 14 | 6.5 | 450 | 100 | 1,100 | 1,050 | 300 | 300 |
| 15 | 4.6 | 450 | 130 | 1,100 | 1,050 | 300 | 300 |
| 32 | 4.6 | 300 | 130 | 1,100 | 1,050 | 300 | 300 |

EXAMPLE 3

The operation of Example 1 was repeated, but with the drier charged (starting from the bottom towards the top of the bed) with:

7 kg of $CaCl_2$ containing 22% of water
5 kg of $CaCl_2$ containing 12% of water
3 kg of $CaCl_2$ containing 21.5% of water.

The operation was carried out in this manner for 12 hours and then 15 kg of $CaCl_2$ containing 1% of water were added on top of the bed. The total operating time was 50 hours.

The results are reported in Table III.

TABLE III

| Time (h) | Residence time (min) | $(H_2O)$ i | ppm o | $(Cl_2)$ i | ppm o | (HCl) i | ppm o |
|---|---|---|---|---|---|---|---|
| 0 | 4.6 | 212 | 160 | 1,100 | 1,050 | 300 | 300 |
| 10 | 10.5 | 255 | 160 | 1,100 | 1,050 | 300 | 300 |
| 12 | 4.6 | 270 | 150 | 1,100 | 1,050 | 300 | 300 |
| 13 | 4.9 | 230 | 25 | 1,100 | 1,200 | 150 | 150 |
| 35 | 4.9 | 265 | 25 | 1,100 | 1,050 | 150 | 150 |
| 40 | 4.9 | 360 | 25 | 1,100 | 1,050 | 150 | 150 |
| 50 | 4.9 | 300 | 25 | 1,260 | 1,300 | 130 | 140 |

EXAMPLE 4

The operation of Example 1 was repeated, but with the drier charged (starting from the bottom towards the top of the bed) with:

7 kg of $CaCl_2$ containing 22% of water
5 kg of $CaCl_2$ containing 12% of water
4 kg of $CaCl_2$ containing 5% of water
14 kg of $CaCl_2$ containing 1% of water.

The results are reported in Table IV.

TABLE IV

| Time (h) | Residence time (min) | $(H_2O)$ i | ppm o | $(Cl_2)$ i | ppm o | (HCl) i | ppm o |
|---|---|---|---|---|---|---|---|
| 10 | 4.5 | 280 | 25 | 1,570 | 1,550 | 240 | 240 |
| 35 | 4.5 | 300 | 25 | 1,550 | 1,550 | 300 | 300 |

EXAMPLE 5 (COMPARATIVE)

Chloromethanes were dried over molecular sieves. 50 g of molecular sieve, namely, 71 ml, were arranged over a height of 540 mm in a glass tube of 13 mm internal diameter and 700 mm in height. The chloromethanes were in a flask and flowed under gravity into the molecular sieve layer at a variable flow rate regulated by a needle valve and were collected in a conical receiver vented into a wash bottle containing concentrated sulfuric acid.

A steady flow rate of chloromethanes was obtained by placing the flask under a constant pressure of nitrogen.

A 3-angstrom potassium sieve was employed in the form of 2-mm beads.

The results are reported in Table V, in which MS stands for Molecular Sieve.

TABLE V

| Liquid tested | Flow rate (l/h) | Linear speed (cm/min) | Space velocity flow rate (l/h) MS vol (l) | $H_2O$ ppm | HCl ppm |
|---|---|---|---|---|---|
| Mixture (by wt.) | | | | | |
| $CH_2Cl_2$: 17% | 1.5 | 19 | 21 | 38 | 4 |
| $CHCl_3$: 60% | 2.0 | 25 | 28 | 38 | 4 |
| $CCl_4$: 23% | 2.5 | 31.5 | 35 | 33 | 4 |
| $H_2O$ = 85 ppm | | | | | |
| HCl = 22 ppm | | | | | |
| Chloromethane mixture | 2.5 | 31.5 | 35 | 30 | 4 |
| as above | 3.0 | 38 | 42 | 18 | 4 |
| $H_2O$ = 145 ppm | 3.5 | 44 | 49 | 18 | 4 |
| HCl = 18 ppm | | | | | |

The space velocity is expressed in liters per hour per liter of sieve.

It was found that HCl was retained, like water, on the molecular sieve.

EXAMPLE 6

Apparatus according to FIG. 1 was employed, in which the column 40, 800 mm in diameter, comprised 35 valve trays and operated at 9 bars absolute. The head temperature was 40° C., the bottom temperature 110° C. The drying agent, $CaCl_2$ with a content of more than 95%, was arranged as a stationary bed in a vessel 50, 2800 mm in diameter, 5800 mm in height.

The condenser was fed with the dry $CH_3Cl$ drier output.

The flowstream 6 contained:
10 to 20% $CH_3Cl$
50-100 ppm $H_2O$
100-500 ppm $Cl_2$
50-500 ppm HCl
80 to 90% $CH_2Cl_2 + CHCl_3 + CCl_4$.

The stream 8 constituted the reflux of the distillation column, containing $CH_3Cl$, HCl, $Cl_2$, the $H_2O$ content of which was lower than 20 ppm.

The stream 7 represents the $CH_3Cl$ extracted from the column, the composition of which was identical to the flow 8.

The stream 9 constitutes the proportion of $CH_3Cl$ which was recycled, of the same composition as the flowstreams 7 and 8.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for recovering halogenated hydrocarbons comprising:
   a. treating a mixture of at least one halogenated hydrocarbon, water and hydrochloric acid to remove a major amount of aid hydrochloric acid and to produce a stream comprising said halogenated hydrocarbon, water and a minor amount of said hydrochloric acid;
   b. treating said stream produced in step (a) to produce a stream comprising said halogenated hydrocarbon, less than about 1% water and less than about 1000 ppm hydrochloric acid and;
   c. intimately contacting said stream produced in step (b) with an effective drying amount of an essentially anhydrous drying agent which comprises (i) a metal sulfate, chloride or perchlorate or (ii) phosphorous pentoxide without concomitantly removing the hydrochloric acid.

* * * * *